United States Patent [19]

Robins et al.

[11] Patent Number: 5,763,419

[45] Date of Patent: Jun. 9, 1998

[54] TREATMENT OF MALIGNANT TUMORS WITH 8-CHLOROADENOSINE 3',5'-CYCLIC MONOPHASPHATE

[75] Inventors: Roland K. Robins, deceased, late of Irvine, Calif., by Lessa Robins, legal representative; Yoon Sang Cho-Chung, Bethesda, Md.

[73] Assignee: ICN Pharmaceuticals, Costa Mesa, Calif.

[21] Appl. No.: 438,537

[22] Filed: May 10, 1995

Related U.S. Application Data

[63] Continuation of Ser. No. 773,990, Oct. 9, 1991, abandoned, which is a continuation of Ser. No. 649,242, Jan. 29, 1991, abandoned, which is a continuation of Ser. No. 393,989, Aug. 14, 1989, abandoned, which is a continuation of Ser. No. 136,407, Dec. 21, 1987, Pat. No. 4,861,873.

[51] Int. Cl.$^6$ .................... A61K 31/70; C07H 19/22
[52] U.S. Cl. .................... 514/47; 536/26.13
[58] Field of Search .................... 514/47; 536/26.13

[56] References Cited

U.S. PATENT DOCUMENTS 4,198,489   5/1988   Cho-Chung ........................ 514/47

OTHER PUBLICATIONS

Cho–Chung(II), "Site Selective 8–Chloro–Cyclic Adenosine 3', 5'–Monophosphate as a Biologic Modulator of Cancer: Restoration of Normal Control Mechanisms," *J. Nat. Cancer Inst. USA*, 81(13), 982–987 (1989).

Avery et al., "Treatment of Murine and Human Neoplasms In Vivo with the Site–Selective cAMP Analog, 8–Cl–cAMP," *Proc. Am. Assoc. Cancer Res.*, Abstr. 1408, vol. 29, 354 (1988).

Parandoosh et al., "Diaclglycerol (DAG) Mass Measurement in Tumor Cells Treated with 8–Chloro and 8–Amino cAMP," *Proc. Am. Assoc. Cancer Res.*, Abstr. 1409, vol. 29, 354 (1988); (formerly cited as Avery et al.).

Rubalcava et al., "8–Chloro and 8–Amino cAMP Translocate Protein Kinase C From Plasma Membrane to Cytosol In Cancer Calls," *Proc. Am. Assoc. Cancer Res.*, Abstr. 1426, vol. 29, 358 (1988).

Ally et al., "Suppression of the Growth in Athymic Mice of Human Lung Carcinomas by 8–Cl–cAMP is Associated With Differential Regulation of the cAMP Receptor Proteins and c–ras Proto–oncogene," *Proc. Am. Assoc. Cancer Res.*, Abstr. 223, vol. 29, 56 (1988).

Katsaros et al., "Transcriptional Activation of the R$^{II}$ cAMP Receptor Protein and cras Proto–oncogene in the Growth Inhibition of Human Colon Cancer Cell Line Treated with 8–Cl–cAMP," *Proc. Am. Assoc. Cancer Res.*, Abstr. 231, vol. 29, 58 (1988).

Katsaros et al., "Site–Selective Cyclic AMP Analogs Provide a New Approach Control of Cancer Cell Growth," *FEBS Letters*, 223(1), 97–103 (1987).

Cho–Chung et al.(I), "Site Selective cAMP Analogs are Cytostatic and Differentiating Agents for a Spectrum of Human Cancer Cell Lines: Potential for Application to Chemotherapy," *Proc. Am. Soc. Clin. Oncology*, 6, Abstr. 62, p. 17, 1987.

Tagliaferri et al.(I), "Reverse Transformation of Harvey Murine Sarcoma Virus–transformed NIH/3T3 Cells by Site–Selective Cyclic AMP Analogs," *J. Biol. Chem.*, 263(1), 409–416 (Jan. 15, 1988(.

Tagliaferri et al.(II), "Synergistic Inhibition of Growth of Breast and Colon Human Cancer Cell Lines by Site–Selective Cyclic AMP Analogues," *Cancer Res.*, 48, 1642–1650 (Mar. 15, 1988).

Tortora et al.(I), "Site–Selective cAMP Analogs at Micromolar Concentrations Induce Growth Arrest and Differentiation of Acute Promyelocytic, Chronic Myelocytic, and Acute Lymphocytic Human Leukemia Cell Lines,"*Blood* 71(1), 230–233 (Jan. 1988).

Houghton et al., "The Suitability and Use of Human Tumor Xenografts," Chapter 42 in *Rodent Tumor Models in Experimental Cancer Therapy*, reports of a meeting held in Oct. 1984, Kallman ed., 1987, Pergamon Press, New York, pp. 199–204.

Steel, "How Well Do Xengrafts Maintain the Therapeutic Response Characteristics of the Source Tumor in the Donor Patient?" Chapter 43 in *Rodent Tumor Models in Experimental Cancer Therapy*, reports of a meeting held in Oct. 1984, Kallman ed., 1987, Pergamon Press, New York, pp. 205–208.

Kallinowski et al., "Blood Flow and Oxygen Consumption of Primary and Xenotransplanted Human Mammary Carcinomas," Chapter 45 in *Rodent Tumor Models in Experimental Cancer Therapy*, reports of a meeting held in Oct. 1984, Kallman ed., 1987, Pergamon Press, New York, pp. 214–217.

Ovejera, "The Use of Human Tumor Xenografts in Large–Scale Drug Screening," Chapter 46 in *Rodent Tumor Models in Experimental Cancer Therapy*, reports of a meeting held in Oct. 1984, Kallman ed., 1987, Pergamon Press, New York, pp. 218–220.

Shorthouse et al., "The Human Tumour Xenograft –A Valid Model in Experimental Chemotherapy?" *Br. J. Surg.*, 67, 715–722 (1980).

Chahinian et al., "Usefulness of the Nude Mouse in Mesothelioma Based on a Direct Patient–Xenograft Comparison," *Cancer*, 68, 558–560 (1991).

*In Vivo Cancer Models*, 1976–1982, U. S. National Institutes of Health Publication No. 84–2635, Feb. 1984, Bethesda, MD.

(List continued on next page.)

*Primary Examiner*—John Kight
*Assistant Examiner*—L. Eric Crane
*Attorney, Agent, or Firm*—Crockett & Fish

[57] ABSTRACT

The compound 8-chloroadenosine 3',5'-cyclic phosphate and its pharmaceutically acceptable salts are used to treat malignant tumors in afflicted hosts.

12 Claims, No Drawings

OTHER PUBLICATIONS

Beardsley, "Trends in Cancer Epidemiology –A War Not Won," *Scientific American*, 270(1), 130–138 (1994).

Rohlff et al., "8–Cl–cAMP Induces Truncation and Down–regulation of the $RI_\alpha$ Subunit and Up–regulation of the $RII_\beta$ Subunit of cAMP–dependent Protein Kinase Leading to Type II Holoenzyme–dependent Growth Inhibition and Differentiation of HL–60 Leukemia Cells," *J. Biol. Chem.*, 268(8), 5774–5782 (Mar. 1993).

Cho–Chung et al. (II), "Suppression of Malignancy Targeting the Intracellular Signal Transducing Proteins of cAMP: The Use of Site–Selective cAMP Analogs, Antisense Strategy, and Gene Transfer," *Life Sciences*, 48(12), 1123–1132 (1991).

Cho–Chung et al. (III), "Regulatory Subunit of cAMP–Dependent Protein Kinase as a Target for Chemotherapy of Cancer and Other Cellular Dysfunctional–Related Diseases," *Pharmacological Therapy*, 60, 265–288 (1993).

Pinto et al., "Inhibition of the Self–Renewal Capacity of Blast Progenitors from Acute Myeloblastic Leukemia Patients by Site–Selective 8–Chloroadenosine 3', 5'–Cyalic Monophosphate," *Proc. Nat. Acad. Sci. USA*, 89, 8884–8888 (Oct. 1992).

Tortora et al.(II), "Differentiation of HL–60 Leukemia by Type I Regulatory Subunit Antisense Oligodeoxynucleotide of cAMP–Dependent Protein Kinase," *Proc. Nat. Acad. Sci. USA*, 88, 2011–2015 (Mar. 1991).

TREATMENT OF MALIGNANT TUMORS WITH 8-CHLOROADENOSINE 3',5'-CYCLIC MONOPHASPHATE

CROSS REFERENCE TO RELATED APPLICATIONS

This application is a continuation of U.S. Ser. No. 07/773, 990, filed Oct. 9, 1991, now abandoned, which is a continuation of U.S. Ser. No. 07/649,242, filed Jan. 29, 1991, now abandoned, which is a continuation of U.S. Ser. No. 07/393, 989, filed Aug. 14, 1989, now abandoned, which is a continuation of U.S. Ser. No. 07/136,407, filed Dec. 21, 1987, now U.S. Pat. No. 4,861,873, the entire contents of which are herein incorporated by reference.

BACKGROUND OF INVENTION

This invention is directed to treating malignant tumors in vivo utilizing the compound 8-chloroadenosine 3',5'-cyclic phosphate.

While the arsenal of chemotherapeutic agents for treating neoplastic diseases includes a number of clinically useful agents, control of malignant tumors in warm blooded animals still remains a much sought after goal.

In a study reported from the People's Republic of China but not confirm elsewhere, 8-bromoadenosine 3',5'-cyclic phosphate was noted as inhibiting the solid form of uterine tumor 14, Ehrlich carcinoma, sarcoma-180 and reticulum-cell sarcoma in mice. An abstract of this study appeared in a Cancergram of the International Cancer Research Data Bank, Series CB14 Number 80/03, March 1980, published by the United States Department Health, Education and Welfare National Institute of Health, National Cancer Institute. In contrast to this report, in other studies 8-bromoadenosine 3',5'-cyclic phosphate has been found to be inactive as an antitumor agent in cell culture.

Contemporaneously with the above report, Y. S. Cho-Chung, *J. Cyclic Nucleotide Res.* 6: 163, 1980, reported certain investigative studies on an antagonistic interaction between estrogen and adenosine 3',5'-cyclic monophosphate (hereinafter alternately referred to as cAMP) and what role this might have in the control of growth of hormone-dependent mammary tumors.

In studying the effects of mediated control of tumor growth by adenosine 3',5'-cyclic phosphate, Cho-Chung has elucidated that cAMP functions by binding to a cAMP receptor protein which has two different cAMP binding sites. The cAMP receptor protein is a regulatory subunit of a cAMP dependent protein kinase. There apparently is site selectivity in binding to one or the other of two sites. This activity can thus be described as site 1-selectivity and site 2-selectivity.

In view of the inability of current cancer chemotherapeutics to successfully control all neoplastic diseases, it is evident that there exists a need for new and additional cancer chemotherapeutic agents.

8-chloroadenosine 3',5'-cyclic phosphate was first reported by inventor R. K. Robins of this invention and his other co-authors in K. Muneyama et al, *J. Carbohyd. Nucleosides Nucleotides*, 1, 55, 1974. It has now been found that 8-chloroadenosine 3',5'-cyclic phosphate (hereinafter alternately also identified as 8-chloro cAMP), exhibits such significant antitumor activity so as to be useful as an antitumor agent in vivo.

BRIEF DESCRIPTION OF THE INVENTION

The present invention relates to the use of 8-chloroadenosine 3',5'-cyclic phosphate (8-chloro cAMP) in treating malignant tumors in warm blooded animals. According to this invention the antitumor properties of 8-chloroadenosine 3',5'-cyclic phosphate are achieved by administering to a warm blooded animal (a mammalian host) a pharmaceutical composition containing as its active ingredient an effective amount of 8-chloroadenosine 3',5'-cyclic phosphate or pharmaceutically acceptable salts thereof.

The methods of the invention are effective in bringing about regression, palliation, inhibition of growth and/or remission of tumors.

8-Chloroadenosine 3',5'-cyclic phosphate or pharmaceutically acceptable salts thereof are useful in treating carcinomas and leukemias. Included in such a class are mammary, colon, bladder, lung, prostate, stomach and pancreas carcinomas and lymphoblastic and myeloid leukemias. 8-Chloroadenosine 3',5'-cyclic phosphate or pharmaceutically acceptable salts thereof are especially useful in treating mammary, colon and lung carcinomas.

8-Chloroadenosine 3',5'-cyclic phosphate and it pharmaceutically acceptable salts are used to treat leukemia in an afflicted host. Thus according to this invention the antileukemic properties of 8-chloroadenosine 3',5'-cyclic phosphate are achieved by administering to an afflicted host an effective amount of a pharmaceutical composition containing as its active ingredient 8-chloroadenosine 3',5'-cyclic phosphate or pharmaceutically acceptable salts thereof.

Further, 8-chloroadenosine 3',5'-cyclic phosphate or pharmaceutically acceptable salts thereof are used to treat carcinoma in an afflicted host. Thus according to the invention the carcinostatic properties of 8-chloroadenosine 3',5'-cyclic phosphate are achieved by administering to an afflicted host an effective amount of a pharmaceutical composition containing as its active ingredient 8-chloroadenosine 3',5'-cyclic phosphate or pharmaceutically acceptable salts thereof.

For use in pharmaceutical compositions of the invention a pharmaceutical carrier would be utilized. Preferably the carrier would be chosen to allow for administration of a suitable concentration of 8-chloroadenosine 3',5'-cyclic phosphate either by oral administration, ophthalmic administration, topical administration, suppository administration or by suitable injection as a solution or suspension into the affected warm blooded animal. The dose and choice of administration of 8-chloroadenosine 3',5'-cyclic phosphate of the invention would be dependent upon the host harboring the malignant tumor, the type of tumor and the tumor site. For injection, 8-chloroadenosine 3',5'-cyclic phosphate of the invention could be administered intravenously, intramuscularly, intracerebrally, subcutaneously or intraperitoneally. Further, for facilitating the use of 8-chloroadenosine 3',5'-cyclic phosphate, a physiologically accepted salt, as for instance the sodium, potassium or ammonium salt, could be used. Presently it is preferred to administer the compound by infusion.

DETAILED DESCRIPTION OF THE INVENTION

8-Chloroadenosine 3',5'-cyclic phosphate of the invention can be prepared as was described in the above referenced paper, K. Muneyama et al, *J. Carbohyd. Nucleosides Nucleotides*, 1, 55 1974, via an 8-bromo intermediate compound or by utilizing the new and improved processes of my prior application Ser. No. 136,407, now U.S. Pat. No. X,XXX,XXX.

For use in pharmaceutical preparations of the invention normally a salt of the 3',5'-cyclic phosphate moiety of 8-chloroadenosine 3',5'-cyclic phosphate would be utilized and would be suitably given to a host as a solution in a suitable carrier. Alternately, the free acid form of the compound could be utilized.

Acceptable salts of the phosphate moiety can be selected from, but not necessarily limited to the group consisting of alkali and alkaline earths, e.g. sodium, potassium, calcium, magnesium, lithium, or ammonium and substituted ammonium, trialklyammonium, dialkylammonium, alklyammonium, e.g. triethylammonium, trimethylammonium, diethylammonium, octylammonium, cetyltrimethylammonium and cetylpridium. Such a salt would preferably be chosen from the group consisting of alkali metal salt, as for instance, a sodium or a potassium salt or an ammonium salt.

In performing the invention, 8-chloroadenosine 3',5'-cyclic phosphate, as a free acid or as a salt, is appropriately mixed with a suitable pharmaceutical carrier which, since the compounds of the invention are water soluble, may be as simple as sterilized water or could be a complex carrier having appropriate agents to suitably mimic certain biological environmental, i.e., pH or salt adjusted for solution suitable for intravenous, intramuscular or other injections.

In selecting a suitable pharmaceutical carrier, consideration of the type of tumor, the site of the tumor and the health and age of the host would be given. 8-Chloroadenosine 3',5'-cyclic phosphate might be appropriately used in the presence of a suitable buffer or as a salt as discussed above.

Preferably, 8-chloroadenosine 3',5'-cyclic phosphate of the invention or a salt thereof would be mixed with an appropriate pharmaceutical carrier such that 8-chloroadenosine 3',5'-cyclic phosphate would be suitably soluble in the carrier. Alternately, however, suspensions, emulsions and other formulations of 8-chloroadenosine 3',5'-cyclic phosphate of the invention could be used where indicated. The pharmaceutical carrier, in addition to having a solubilizing or suspending agent therein, might also include suitable diluents, buffers, surface active agents and other similar agents as are typically used in pharmaceutical carriers. The total composition of the pharmaceutical carrier would, however, be chosen to be compatible with the site of delivery, the concentration of the active ingredient and other parameters as are standard in pharmaceutical industry.

8-Chloroadenosine 3',5'-cyclic phosphate of the invention would be suitably admixed with the pharmaceutical carrier such that it would be present in a concentration of at least 0.1 percent by weight of the total composition. Preferably, it would be present in the pharmaceutical carrier at a concentration of about 10% to about 90% by weight of the total composition.

Based on present studies, effective amounts of 8-chloroadenosine 3',5'-cyclic phosphate typically would range from about 13 milligrams per kilogram per day (mg/kg/day) of the total body weight of the treated warm blooded animal to about 288 mg/kg/day. Preferably, the range would be from 22 mg/kg to about 173 mg/kg/day. As with other factors noted above, the amount of 8-chloroadenosine 3',5'-cyclic phosphate utilized in treating an afflicted animal would take into account parameters such as the type of tumor, the tumor site, the form of administering of and the physical size and condition of the host. In any event, the actual amount should be sufficient to provide a chemotherapeutically effective amount of the agent in the host in a convenient volume, which will be readily within the ability of those skilled in the art to determine given the disclosure herein.

The 8-chloroadenosine 3',5'-cyclic phosphate of the invention can be given as single doses or as multiple doses divided into sub-doses given daily or over a period of days. As will be evident from the examples below, 8-chloroadenosine 3',5'-cyclic phosphate of the invention exhibits certain enhanced responses when administered an an infusion and, as such, this will be taken in to account in the optimization of a dosage schedule as is well within the skill of the art given the disclosure herein.

The following examples are given for use of 8-chloroadenosine 3',5'-cyclic phosphate of the invention as a therapeutic agent against neoplastic diseases. In these examples the efficacy of 8-chloroadenosine 3',5'-cyclic phosphate as an antitumor agent is demonstrated by using standard tests against certain malignant tumors including human tumors including solid tumors.

These standard tests utilize protocols developed under the auspices of the Developmental Therapeutic Program, Division of Cancer Treatment, National Cancer Institute, Bethesda, Md., as set forth in *In Vitro Cancer Models*, National Institute of Health Publications No 84-2635, February 1984, United States Department of Health and Human Services, Public Health Service, National Institute of Health.

Staging, growth and testing of tumors was done as is set forth in this publication. The mode of administration and delivery of 8-chloroadenosine 3',5'-cyclic phosphate, however, deviated slightly from these protocols and is as is set forth in each individual example. Evaluation protocols with respect to activity of 8-chloroadenosine 3',5'-cyclic phosphate as an anti-tumor agent, however, follow the criteria as is defined in the above referenced publication.

For the purposes of these examples certain standard abbreviations are utilized as follows: i.p.=intraperitoneal; qd=once a day; mg/kg/day=milligrams per kilograms per day; and No.=number. Further the nomenclature "First-Last" means the first minus the last.

In the example utilizing L1210 as the test tumor cell line, the test results are indicated as %T/C. According to protocols of the National Cancer Institute for the L1210 tumor line, a %T/C value greater than 125% is considered as having statistically meaningful activity. For examples of antitumor properties against solid human tumor cell lines, test results are given as change in mean tumor weight. This is expressed in two ways. If there was an increase in tumor weight the results are expressed as δT/δC. However, if there was a net negative change in tumor weight the results are expressed as δT/T. These two ways of data expressions again follow the protocols and criteria set forth as noted above by the National Cancer Institute.

EXAMPLE 1

8-chloroadenosine 3',5'-cyclic phosphate as a sodium salt was tested utilizing non-tumor bearing $BDF_1$ mice to establish a lethal toxicity for this drug. For this test the drug was delivered i.p. by a bolus injection given as a single dose on day 1. As is evident from Table 1 below, at 104 milligrams per kilograms per injection there were no toxic deaths. At a level of 173 milligrams per kilograms per injection there was a 40 percent toxic death and at 288 milligrams per kilograms per injection the compound exhibited 100 percent lethal toxicity. As will be evident in other examples below, when the compound is delivered by infusion, the test animals tolerated a higher dose of drug before lethal toxicity was seen.

TABLE 1

Influence of 8-Cl-cAMP Na⁺ on the life span of non-tumor BDF₁ mice when delivered i.p. by bolus injection

| Dosage mg/kg/inj | Route and schedule of delivery | Toxic deaths[1] No. killed/No. treated |
|---|---|---|
| 480 | ip: qd, day 1 | 5/5 |
| 288 | ip: qd, day 1 | 5/5 |
| 173 | ip: qd, day 1 | 2/5 |
| 104 | ip: qd, day 1 | 0 |
| 62 | ip: qd, day 1 | 0 |
| 37 | ip: qd, day 1 | 0 |
| 22 | ip: qd, day 1 | 0 |

[1]When delivered qd, day 1 to non-tumor BDF₁ mice, the 480 and 288 mg/kg dosages of 8-Cl-cAMP Na⁺ were lethally toxic for all treated mice. The 173 mg/kg dosage killed 2 of 5 mice and lower dosages were not lethally toxic.

EXAMPLE 2

The activity of 8-chloroadenosine 3',5'-cyclic phosphate against L1210 inoculated BDF₁ mice was determined by both bolus injection and by infusion. As shown in Table 2 below, when delivered by bolus injection there was insignificant activity, however, when infused into a test animal in a dose range of from 22 mg to 173 mg/kg/day, 8-chloroadenosine 3',5'-cyclic phosphate exhibited significant antitumor activity. Further, the toxicity was determined for the infusion test animals. As is also evident from Table 2 when infused at 173 mg/kg/day the compound was not toxic, however, when infused at the 288 mg/kg/day level both activity and toxicity are noted and at higher levels, at 480 and 800 mg/kg/day, the compound is lethally toxic.

The results of Table 2 indicate that 8-chloroadenosine 3',5'-cyclic phosphate is an effective antitumor agent against L1210 inoculated mice when infused into the test animals. Further the compound demonstrated a dose response for this activity. As was indicated above, a %T/C of greater than 125 indicates significant activity.

TABLE 2

Influence of 8-Cl-cAMP Na⁺ on the postinoculation lifespan of L1210-inoculated BDF₁ mice[1] when infused or delivered by bolus injection

| Dosage (mg/kg/day) | Route and schedule of delivery | Postinoculation lifespan[2] % (T/C) |
|---|---|---|
| 104 | ip: qd, day 1–7 | 98 |
| 62 | ip: qd, day 1–7 | 103 |
| 37 | ip: qd, day 1–7 | 93 |
| 22 | ip: qd, day 1–7 | 103 |
| 800 | ip: 24-hr infusion, day 1–5 | 62 toxic[3] |
| 480 | ip: 24-hr infusion, day 1–5 | 93 toxic[3] |
| 288 | ip: 24-hr infusion, day 1–5 | 128 toxic[3] |
| 173 | ip: 24-hr infusion, day 1–5 | 131 |
| 104 | ip: 24-hr infusion, day 1–5 | 137 |
| 62 | ip: 24-hr infusion, day 1–5 | 137 |
| 37 | ip: 24-hr infusion, day 1–5 | 126 |
| 22 | ip: 24-hr infusion, day 1–5 | 126 |
| 13 | ip: 24-hr infusion, day 1–5 | 113 |
| 48 | ip: 24-hr infusion, day 1–5 | 100 |
| 17 | ip: 24-hr infusion, day 1–5 | 100 |
| 0.6 | ip: 24-hr infusion, day 1–5 | 100 |

[1]Mice were inoculated i.p. with 1 × 10⁶ cells of murine leukemia L1210 24-hr before first treatment. Each treatment group consisted of 5 mice. Twenty control mice that received a 0.9% solution of NaCl lived 6.2 ± days.
[2]Significant activity indicated at % T/C > 125.
[3]When infused, the 800 and 480 mg/kg dosages of 8-Cl-cAMP Na⁺ were lethally toxic for all treated mice while the 288 mg/kg dosage killed 2 of 5 mice.

8-chloroadenosine 3',5'-cyclic phosphate was tested and has shown activity against a variety of solid human tumor cell lines. In the tests of Examples 3 through 6 shown in Tables 3 through 6, what is being measured is tumor regression size and not increase in life span of the test animal. This expression follows the accepted National Cancer Institute protocol procedures for respective solid tumors cell lines which were tested.

EXAMPLE 3

In this example, 8-chloroadenosine 3',5'-cyclic phosphate given by infusion was tested against human mammary carcinoma in athymic mice. In a first study shown in the upper portion of Table 3a, at the dose levels given, a mean reduction in tumor weight is evident. As such the change in this mean reduction in tumor weight, following the above noted National Cancer Institute protocols, is expressed as δT/T. In the study shown in the lower portion of Table 3a, at lower dose levels, the δ weight between the starting tumor weight and the final tumor weight was greater than unity and as such again following the established protocols, the results are shown as δT/δC.

Any value for δT/δC or δT/T which is below 25 is considered by the National Cancer Institute protocols as indicative of significant activity. As is evident from Table 3a significant activity was indicated over a large dosage range of from 22 mg/kg up to and including 173 mg/kg (the highest dose included in this example).

TABLE 3a

Influence of intraperitoneally infused 8-Cl-cAMP Na⁺ on the growth in athymic mice of human mammary carcinoma MX-1[1]

| Dosage (mg/kg/day) | Initial Mean Weight (mg) | δ First – Last Tumor Weight[2] | Change in Mean Tumor Weight[3] (δT/δC or δT/T) |
|---|---|---|---|
| 173 | 375 | −39 | −10.4[4] |
| 104 | 346 | −23 | −6.7[4] |
| 62 | 337 | −49 | −14.5[4] |
| 0 | 334 | 215 | — |
| 37 | 194 | 16 | 6[5] |
| 22 | 201 | 76 | 29[5] |

TABLE 3a-continued

Influence of intraperitoneally infused 8-Cl-cAMP Na+ on the growth in athymic mice of human mammary carcinoma MX-1[1]

| Dosage (mg/kg/day) | Initial Mean Weight (mg) | δ First – Last Tumor Weight[2] | Change in Mean Tumor Weight[3] (δT/δC or δT/T) |
|---|---|---|---|
| 13 | 216 | 95 | 37[5] |
| 0 | 204 | 259 | — |

[1]Tumor fragments (≈14 mg) were implanted subcutaneously in the thigh region of athymic CD-1 female mice. Three weeks later the tumors were staged and treatment lasting 7 days was started, each treatment group consisted of 7 mice.
[2]Tumor measurements recorded on the initial day of treatment (staging day) and again on day 8 were used to calculate mean tumor weight changes and δT/δC or δT/T.
[3]δT/δC utilized for positive First – Last tumor weights and δT/T utilized for negative First – Last tumor weights.
[4]δT/T
[5]δT/δC The mean tumor weight at each dose shown in Table 3a for all the test animals at days 1 and 8 are indicated in Table 3b.

TABLE 3b

Tumor weights of human mammary carcinoma MX-1 tumors in athymic mice intraperitoneally infused with 8-Cl-cAMP Na+

| Dosage (mg/kg/day) | Initial Mean Weight (mg) Day 1 | Mean Tumor Weight (mg) Day 8 |
|---|---|---|
| 173 | 375 | 336 |
| 104 | 346 | 317 |
| 62 | 337 | 288 |
| control | 334 | 549 |
| 37 | 194 | 210 |
| 22 | 201 | 277 |
| 13 | 216 | 311 |
| control | 204 | 463 |

EXAMPLE 4

8-chloroadenosine 3',5'-cyclic phosphate was further tested in athymic mice against human colon carcinoma LoVo. As per Example 8, administration was also by infusion. The results of this test are shown in Table 4a below. The mean change in tumor weight is indicated either as δT/δC for the positive value or δT/T for the negative values as was discussed with respect to Example 3 above. As is evident at the 37 and 62 kg/mg dosage the compound exhibited significant activity.

TABLE 4a

Influence of intraperitoneally infused 8-Cl-cAMP Na+ on the growth in athymic mice of human colon carcinoma LoVo[1]

| Dosage (mg/kg/day) | Initial Mean Weight (mg) | δ First – Last Tumor Weight[2] | Change in Mean Tumor Weight[3] (δT/δC or δT/T) |
|---|---|---|---|
| 104 | 288 | 29 | 35[4] |
| 62 | 293 | –3 | –1.0[5] |

TABLE 4a-continued

Influence of intraperitoneally infused 8-Cl-cAMP Na+ on the growth in athymic mice of human colon carcinoma LoVo[1]

| Dosage (mg/kg/day) | Initial Mean Weight (mg) | δ First – Last Tumor Weight[2] | Change in Mean Tumor Weight[3] (δT/δC or δT/T) |
|---|---|---|---|
| 37 | 288 | –4 | –1.4[5] |
| 0 | 292 | 84 | — |

[1]Tumor fragments (≈14 mg) were implanted subcutaneously in the thigh region of athymic CD-1 female mice. Three weeks later the tumors were staged and treatment lasting 7 days was started, each treatment group consisted of 7 mice.
[2]Tumor measurements recorded on the initial day of treatment (staging day) and again on day 8 were used to calculate mean tumor weight changes and δT/δC or δT/T.
[3]δT/δC utilized for positive First – Last tumor weights and δT/T utilized for negative First – Last tumor weights.
[4]δT/T
[5]δT/δC The mean tumor weight for each dose shown in Table 4a for all the test animals at days 1 and 8 are indicated in Table 4b.

TABLE 4b

Tumor weights of human colon carcinoma LoVo tumors in athymic mice intraperitoneally infused with 8-Cl-cAMP Na+

| Dosage (mg/kg/day) | Initial Mean Weight (mg) Day 1 | Mean Tumor Weight (mg) Day 8 |
|---|---|---|
| 104 | 288 | 317 |
| 62 | 293 | 290 |
| 37 | 288 | 284 |
| control | 292 | 376 |

EXAMPLE 5

8chloroadenosine 3',5'-cyclic phosphate was further tested in athymic mice against human mammary carcinoma MDA-MB-231. The test was also done using infusion as the route of administration. The results of this test are shown in Table 5a below. The compound exhibited significant activity at the dose levels of 62 and 104 mg/kg/day. Further while it did not exhibit significant activity at all dose levels it did show a linearity of response throughout the tested dosage range against this tumor line.

TABLE 5a

Influence of intraperitoneally infused 8-Cl-cAMP Na+ on the growth in athymic mice of human mammary carcinoma MDA-MB-231[1]

| Dosage (mg/kg/day) | Initial Mean Weight (mg) | δ First – Last Tumor Weight[2] | Change in Mean Tumor Weight[3] δT/δC |
|---|---|---|---|
| 104 | 367 | 66 | 18 |
| 62 | 375 | 96 | 26 |

TABLE 5a-continued

Influence of intraperitoneally infused 8-Cl-cAMP Na+
on the growth in athymic mice of human mammary carcinoma
MDA-MB-231[1]

| Dosage (mg/kg/day) | Initial Mean Weight (mg) | δ First – Last Tumor Weight[2] | Change in Mean Tumor Weight[3] δT/δC |
|---|---|---|---|
| 37 | 367 | 149 | 41 |
| 0 | 361 | 365 | — |

[1]Tumor fragments (≈14 mg) were implanted subcutaneously in the thigh region of athymic CD-1 female mice. Three weeks later the tumors were staged and treatment lasting 7 days was started, each treatment group consisted of 7 mice.
[2]Tumor measurements recorded on the initial day of treatment (staging day) and again on day 8 were used to calculate mean tumor weight changes and δT/δC or δT/T.
[3]δT/δC utilized for positive First – Last tumor weights.

The mean tumor weight for each dose shown in Table 5a for all the test animals at days 1 and 8 are indicated in Table 5b.

TABLE 5b

Tumor weights of human mammary carcinoma MDA-MB-231 tumors in athymic mice intraperitoneally infused with 8-Cl-cAMP Na+

| Dosage (mg/kg/day) | Initial Mean Weight (mg) Day 1 | Mean Tumor Weight (mg) Day 8 |
|---|---|---|
| 104 | 367 | 433 |
| 62 | 375 | 471 |
| 37 | 367 | 516 |
| control | 361 | 726 |

EXAMPLE 6

8-chloroadenosine 3',5'-cyclic phosphate was further tested in athymic mice against human lung carcinoma LX1. As per the results shown in Table 6a below, the compound exhibited significant activity at a dose range of from 37 mg to 104 mg/kg/day. For this test infusion was only for 5 days as opposed to the 7 days used for the previous solid tumor tests of Examples 3, 4 and 5. Further, as per Example 3 the positive mean tumor weights results are shown as δT/δC and negative mean tumor weights as δT/T. It is significant to note at both the 62 and 104 mg dosage there was a high degree of tumor weight loss as opposed to only inhibition of tumor growth, i.e. at the 62 and 104 mg dose levels there was tumor regression.

TABLE 6a

Influence of intraperitoneally infused 8-Cl-cAMP Na+
on the growth in athymic mice of human lung carcinoma LX-1[1]

| Dosage (mg/kg/day) | Initial Mean Weight (mg) | δ First – Last Tumor Weight[2] | Change in Mean Tumor Weight[3] δT/δC |
|---|---|---|---|
| 104 | 324 | −54 | −16.7[4] |
| 62 | 327 | −50 | −15.3[4] |
| 37 | 330 | 11 | 6[5] |
| 0 | 332 | 183 | — |

[1]Tumor fragments (≈14 mg) were implanted subcutaneously in the thigh region of athymic CD-1 female mice. Three weeks later the tumors were staged and treatment lasting 5 days was started, each treatment group consisted of 7 mice.
[2]Tumor measurements recorded on the initial day of treatment (staging day) and again on day 8 were used to calculate mean tumor weight changes and δT/δC or δT/T.
[3]δT/δC utilized for positive First – Last tumor weights and δT/T utilized for negative First – Last tumor weights.
[4]δT/T
[5]δT/δC The mean tumor weight for each dose shown in Table 6a for all the test animals at days 1 and 8 are indicated in Table 6b.

TABLE 6b

Tumor weights of human lung carcinoma LX-1 tumors in athymic mice intraperitoneally infused with 8-Cl-cAMP Na+

| Dosage (mg/kg/day) | Initial Mean Weight (mg) Day 1 | Mean Tumor Weight (mg) Day 8 |
|---|---|---|
| 104 | 324 | 270 |
| 62 | 327 | 277 |
| 37 | 330 | 341 |
| control | 332 | 515 |

For delivery to a host inflicted with a neoplastic disease 8-chloroadenosine 3',5'-cyclic phosphate of the invention can be formulated in various formulations to prepare pharmaceutical compositions containing 8-chloroadenosine 3',5'-cyclic phosphate of the invention as active ingredient. The following illustrative examples are given for the formulations of such pharmaceutical compositions utilizing the sodium salt of 8-chloroadenosine 3',5'-cyclic phosphate.

In these examples, Pharmaceutical Preparative Example A illustrates the use of 8-chloroadenosine 3',5'-cyclic phosphate sodium salt in injectables suitable for intravenous or other types of injection into the host animal. Pharmaceutical Preparative Example B is directed to an oral syrup preparation, Pharmaceutical Preparative Example C to an oral capsule preparation and Pharmaceutical Preparative Example D to oral tablets. Pharmaceutical Preparative Example E is directed to use of 8-chloroadenosine 3',5'-cyclic phosphate sodium salt in suitable suppositories. For Pharmaceutical Preparative Examples A through E, the ingredients are listed followed by the methods of preparing the composition.

EXAMPLE A

| INJECTABLES | |
|---|---|
| 8-chloroadenosine 3',5'-cyclic phosphate sodium salt | 250 mg–1000 mg |
| Water for Injection USP q.s. | |

The 8-chloroadenosine 3',5'-cyclic phosphate sodium salt is dissolved in the water and passed through a 0.22μ filter. The filtered solution is added to ampoules or vials, sealed and sterilized.

EXAMPLE B

| SYRUP 250 mg Active ingredient/5 ml syrup | |
|---|---|
| 8-chloroadenosine 3',5'-cyclic phosphate sodium salt | 50.0 g |
| Purified Water USP q.s. or | 200 ml |
| Cherry Syrup q.s. ad | 1000 ml |

The 8-chloroadenosine 3',5'-cyclic phosphate sodium salt is dissolved in the water and to this solution the syrup is added with mild stirring.

EXAMPLE C

| CAPSULES 100 mg 250 mg or 500 mg | |
|---|---|
| 8-chloroadenosine 3',5'-cyclic phosphate sodium salt | 500 g |
| Lactose USP, Anhydrous q.s. or | 200 g |
| Sterotex Powder HM | 5 g |

Combine the 8-chloroadenosine 3',5'-cyclic phosphate sodium salt and the Lactose in a twin-shell blender equipped with an intensifier bar. Tumble blend for two minutes, followed by blending for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg, 352.5 mg or 705 mg of the blend, respectively, for the 100 mg, 260 mg and 500 mg containing capsules.

EXAMPLE D

| TABLETS 100 mg, 200 mg or 500 mg | |
|---|---|
| 8-chloroadenosine 3',5'-cyclic phosphate | 500 g |
| Corn Starch NF | 200.0 g |
| Cellulose Microcrystalline | 46.0 g |
| Sterotex Powder HM | 4.0 g |
| Purified Water q.s. or | 300.0 ml |

Combine the corn starch, the cellulose and the 8-chloroadenosine 3',5'-cyclic phosphate together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen at medium speed. The Sterotex Powder is added to a portion of the mix and passed through a #30 screen and added back to the milled mixture and the total blended for five minutes by drum rolling. Compressed tables of 150 mg, 375 mg and 750 mg respectively, of the total mix are formed with appropriate sized punches for the 100 mg, 250 mg or 500 mg containing tables.

EXAMPLE E

| SUPPOSITORIES 250 mg, 500 mg or 1000 mg per 3 g | | | |
|---|---|---|---|
| 8-chloroadenosine 3',5'-cyclic phosphate sodium salt | 250 mg | 500 mg | 1000 mg |
| Polyethylene Glycol 1540 | 1925 mg | 1750 mg | 1400 mg |
| Polyethylene Glycol 8000 | 825 mg | 750 mg | 600 mg |

The Polyethylene Glycol 1540 and the Polyethylene Glycol 8000 are melted together at 60° C. The 8-chloroadenosine 3',5'-cyclic phosphate sodium salt is dissolved into the melt and the resultant product is molded at 25° C. into appropriate suppositories.

It is claimed:

1. A method of treating tumors in warm blooded animals in need thereof comprising:
   administering to said warm blooded animals a therapeutically effective amount of a composition containing as its active component the compound 8-chloroadenosine 3',5'-cyclic phosphate and pharmaceutically acceptable salts thereof.

2. The method of claim 1 wherein:
   said composition is administered to said warm blooded animal by injection.

3. The method of claim 1 wherein:
   said composition is administered to said warm blooded animal by infusion of said composition into said warm blooded animal.

4. The method of claim 1 wherein:
   said composition is administered in an amount to deliver from about 13 mg/kg/day to about 288 mg/kg/day of said 8-chloroadenosine 3',5'-cyclic phosphate to said warm blooded animal.

5. The method of claim 4 wherein:
   said 8-chloroadenosine 3',5'-cyclic phosphate is delivered in an amount of from about 22 mg/kg/day to about 173 mg/kg/day.

6. A method of treating leukemia in a host comprising:
   administering to said host afflicted with leukemia an antileukemic composition containing as its active ingredient a therapeutically effective amount of the compound 8-chloroadenosine 3',5'-cyclic phosphate and pharmaceutically acceptable salts thereof.

7. A method of treating carcinoma in an afflicted host comprising:
   administering to said host a composition containing as its active ingredient a carcinostatic effective amount of the compound 8-chloroadenosine 3',5'-cyclic phosphate and pharmaceutically acceptable salts thereof.

8. The method of claim 7 wherein:
   said carcinoma is a human carcinoma.

9. The method of claim 7 wherein:
   said carcinoma is selected from the group consisting of mammary, colon, bladder, lung, prostate, stomach and pancreas carcinomas.

10. The method of claim 7 wherein:

said carcinoma is selected from the group consisting of mammary, colon and lung carcinomas.

11. A method of treating human tumors comprising:

administering to a host afflicted with said human tumor an antitumor composition containing as its active ingredient a antitumor effective amount of the compound 8-chloroadenosine 3',5'-cyclic phosphate and pharmaceutically acceptable salts thereof.

12. The method of claim 11 wherein:

said human tumor is a solid tumor.

* * * * *